US012023007B2

(12) United States Patent
On et al.

(10) Patent No.: US 12,023,007 B2
(45) Date of Patent: Jul. 2, 2024

(54) ENDOSCOPE APPARATUS AND OPERATION METHOD OF ENDOSCOPE APPARATUS

(71) Applicant: OLYMPUS CORPORATION, Tokyo (JP)

(72) Inventors: Seigo On, Hachioji (JP); Yasunori Morita, Hachioji (JP); Masashi Hirota, Hachioji (JP); Jumpei Takahashi, Tokyo (JP)

(73) Assignee: OLYMPUS CORPORATION, Tokyo (JP)

( * ) Notice: Subject to any disclaimer, the term of this patent is extended or adjusted under 35 U.S.C. 154(b) by 556 days.

(21) Appl. No.: 17/133,793

(22) Filed: Dec. 24, 2020

(65) Prior Publication Data
US 2021/0145266 A1 May 20, 2021

Related U.S. Application Data

(63) Continuation of application No. PCT/JP2018/030434, filed on Aug. 16, 2018.

(51) Int. Cl.
*A61B 1/06* (2006.01)
*A61B 1/00* (2006.01)
*A61B 1/04* (2006.01)

(52) U.S. Cl.
CPC ...... *A61B 1/0669* (2013.01); *A61B 1/000094* (2022.02); *A61B 1/0005* (2013.01); *A61B 1/044* (2022.02); *A61B 1/0638* (2013.01)

(58) Field of Classification Search
CPC .......... A61B 1/00009; A61B 1/000094; A61B 1/000095; A61B 1/00045; A61B 1/00186;
(Continued)

(56) References Cited

U.S. PATENT DOCUMENTS 10,448,816 B2 * 10/2019 Moriya ................ A61B 1/0638
11,103,123 B2 *  8/2021 Moriya ................ A61B 1/0638
(Continued)

FOREIGN PATENT DOCUMENTS

JP    2012-125461 A    7/2012
JP    2016-32494 A     3/2016
(Continued)

OTHER PUBLICATIONS

International Search Report dated Oct. 16, 2018 issued in PCT/JP2018/030434, together with an English-language translation.
(Continued)

*Primary Examiner* — Ryan N Henderson
(74) *Attorney, Agent, or Firm* — Scully, Scott, Murphy & Presser, P.C.

(57) ABSTRACT

An endoscope apparatus includes: a light source device alternately emitting a first illumination light group including green light and a second illumination light group not including the green light; an image sensor including color filters of a plurality of colors; and a processing circuit. The processing circuit generates a display image on the basis of an image obtained with the first illumination light group and an image obtained with the second illumination light group. The first illumination light group further includes blue narrowband light together with the green light. The processing circuit generates a green channel image in the display image on the basis of a green image and a blue narrowband image.

18 Claims, 8 Drawing Sheets

(58) Field of Classification Search
CPC ......... A61B 1/045; A61B 1/05; A61B 1/0638;
A61B 1/0684; A61B 1/00043; A61B
1/0005; A61B 1/043; A61B 1/044; A61B
1/046; A61B 1/063; A61B 1/653; A61B
1/0655; A61B 1/0661; A61B 1/0669;
G06T 2207/10024; G06T 2207/10028;
G06T 2207/10068

See application file for complete search history.

(56) References Cited

U.S. PATENT DOCUMENTS

| | | | |
|---|---|---|---|
| 2003/0028078 A1* | 2/2003 | Glukhovsky | A61B 1/0676 600/109 |
| 2010/0278404 A1* | 11/2010 | Takei | G06T 5/50 382/128 |
| 2012/0154566 A1 | 6/2012 | Kaku | |
| 2012/0157775 A1* | 6/2012 | Yamaguchi | A61B 5/14551 600/180 |
| 2012/0218394 A1* | 8/2012 | Yoshino | A61B 1/0638 348/222.1 |
| 2012/0220840 A1* | 8/2012 | Morita | A61B 1/0638 600/109 |
| 2013/0329027 A1* | 12/2013 | Igarashi | A61B 1/0638 348/68 |
| 2015/0094530 A1* | 4/2015 | Moriya | F21V 5/04 600/109 |
| 2015/0094538 A1* | 4/2015 | Terakawa | A61B 1/000094 600/160 |
| 2016/0089011 A1* | 3/2016 | Shiraishi | A61B 1/044 348/71 |
| 2016/0270643 A1* | 9/2016 | Sasaki | A61B 1/000095 |
| 2017/0311774 A1* | 11/2017 | Hirota | A61B 5/0084 |
| 2018/0000317 A1* | 1/2018 | Mitamura | H04N 23/84 |
| 2018/0153386 A1* | 6/2018 | Omori | A61B 1/0005 |
| 2019/0110673 A1* | 4/2019 | Ito | A61B 1/00096 |
| 2019/0208986 A1* | 7/2019 | Saito | A61B 1/000094 |
| 2019/0335979 A1* | 11/2019 | Moriya | A61B 1/0638 |
| 2019/0387964 A1* | 12/2019 | Kobayashi | A61B 1/0661 |
| 2020/0099844 A1* | 3/2020 | Shinji | A61B 1/0605 |
| 2020/0170492 A1* | 6/2020 | Kuramoto | A61B 5/489 |
| 2020/0178781 A1* | 6/2020 | Tabata | A61B 1/063 |

FOREIGN PATENT DOCUMENTS

| | | | | |
|---|---|---|---|---|
| JP | 2016032494 A | * | 3/2016 | |
| JP | 2016-067778 A | | 5/2016 | |
| JP | 2016-77756 A | | 5/2016 | |
| JP | 2016067778 A | * | 5/2016 | ......... A61B 1/00009 |
| JP | 2016-131837 A | | 7/2016 | |
| JP | 2018-038675 A | | 3/2018 | |

OTHER PUBLICATIONS

Japanese Office Action dated Dec. 14, 2021 received in 2020-537335.

* cited by examiner

ENDOSCOPE APPARATUS AND OPERATION METHOD OF ENDOSCOPE APPARATUS

CROSS REFERENCE TO RELATED APPLICATION

This application is a continuation of International Patent Application No. PCT/JP2018/030434, having an international filing date of Aug. 16, 2018, which designated the United States, the entirety of which is incorporated herein by reference.

BACKGROUND

A frame sequential method of sequentially emitting a plurality of illumination lights each having a different wavelength is known for use by endoscope apparatuses. This method captures images based on each emitted illumination light using a monochrome image sensor and combines these images corresponding to the respective wavelengths to generate a display image. Also, Japanese Unexamined Patent Application Publication No. 2012-125461 discloses a method of capturing a white light image and a narrowband image and adding information obtained from the narrowband image to the white light image.

SUMMARY

According to one aspect of the disclosure, there is provided an endoscope apparatus comprising:
 a light source device alternately emitting a first illumination light group and a second illumination light group, the first illumination light group including green light with a green wavelength band, the second illumination light group not including the green light;
 an image sensor including color filters of a plurality of colors; and
 a processing circuit that generates a display image, on the basis of an image captured by the image sensor with the first illumination light group emitted and an image captured by the image sensor with the second illumination light group emitted, wherein
 the first illumination light group further includes blue narrowband light together with the green light, the blue narrowband light corresponding to a narrowband in a blue wavelength band, and
 the processing circuit generates a green channel image in the display image, on the basis of a green image obtained with the green light and a blue narrowband image obtained with the blue narrowband light.

According to another aspect of the disclosure, there is provided an endoscope apparatus comprising:
 a light source device alternately emitting a first illumination light group and a second illumination light group, the first illumination light group including green light with a green wavelength band, the second illumination light group not including the green light;
 an image sensor including color filters of a plurality of colors; and
 a processing circuit that generates a display image, on the basis of an image captured by the image sensor with the first illumination light group emitted and an image captured by the image sensor with the second illumination light group emitted, wherein
 the first illumination light group further includes red narrowband light together with the green light, the red narrowband light corresponding to a narrowband in a red wavelength band, and
 the processing circuit generates a green channel image in the display image, on the basis of a green image obtained with the green light and a red narrowband image obtained with the red narrowband light.

According to another aspect of the disclosure, there is provided an operation method of an endoscope apparatus including an image sensor having color filters of a plurality of colors, the method comprising:
 alternately emitting a first illumination light group and a second illumination light group, the first illumination light group including green light with a green wavelength band and blue narrowband light corresponding to a narrowband in a blue wavelength band, the second illumination light group not including the green light;
 generating a display image on the basis of an image captured by the image sensor with the first illumination light group emitted and an image captured by the image sensor with the second illumination light group emitted; and
 in generating the display image, generating a green channel image in the display image on the basis of a green image obtained with the green light and a blue narrowband image obtained with the blue narrowband light.

DESCRIPTION OF EXEMPLARY EMBODIMENTS

Figure 1:
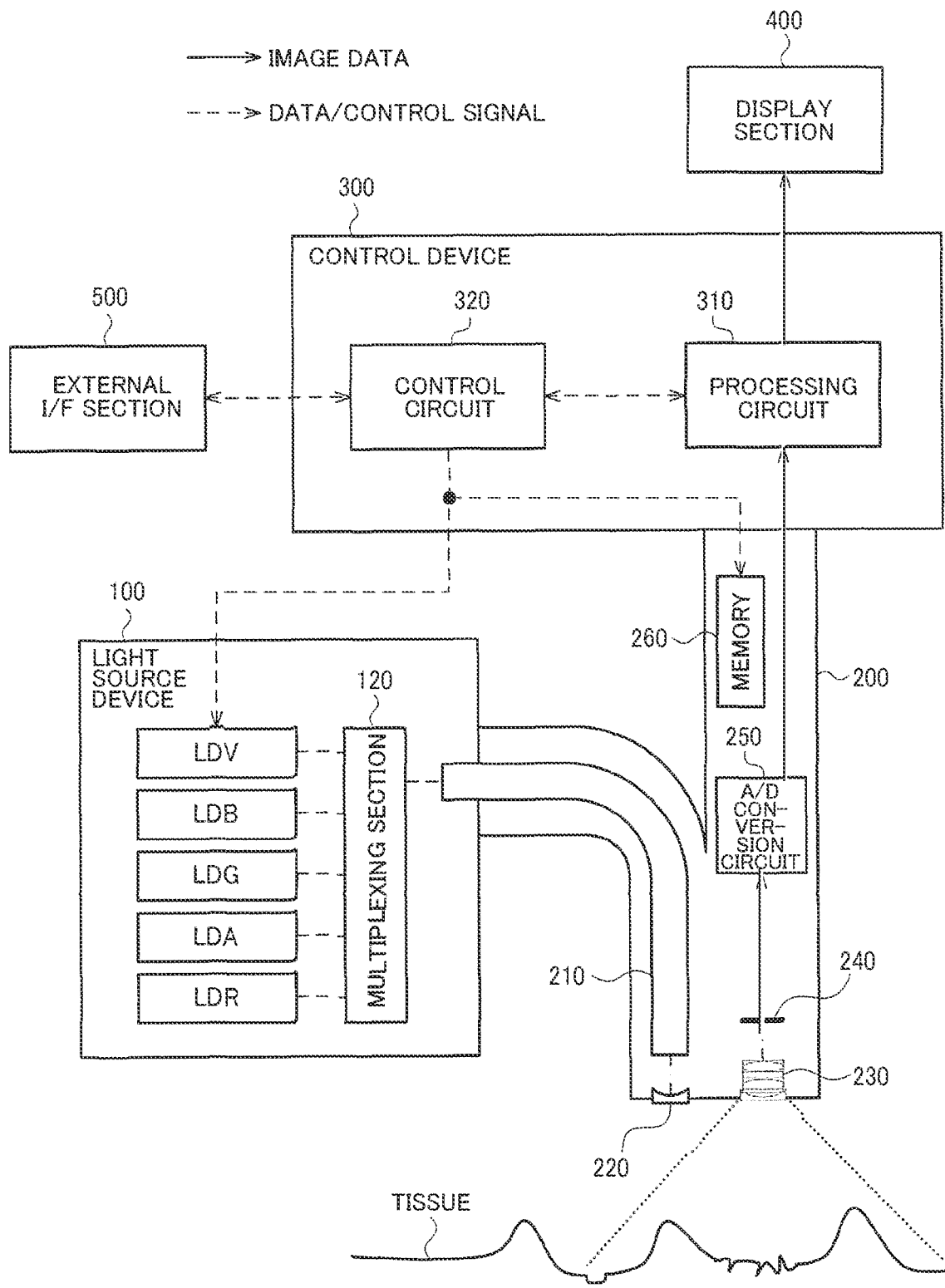
FIG. 1 illustrates a configuration example of an endoscope apparatus.

The following disclosure provides many different embodiments, or examples, for implementing different features of the provided subject matter. These are, of course, merely examples and are not intended to be limiting. In addition, the disclosure may repeat reference numerals and/or letters in the various examples. This repetition is for the purpose of simplicity and clarity and does not in itself dictate a relationship between the various embodiments and/or configurations discussed. Further, when a first element is described as being "connected" or "coupled" to a second element, such description includes embodiments in which the first and second elements are directly connected or coupled to each other, and also includes embodiments in which the first and second elements are indirectly connected or coupled to each other with one or more other intervening elements in between.

1. Endoscope Apparatus

FIG. 1 illustrates a configuration example of an endoscope apparatus. The endoscope apparatus includes an insertion section 200, a control device 300, a display section 400, an external I/F section 500, and a light source device 100. Non-limiting examples of the endoscope apparatus may include a flexible scope used for a digestive tract and the like, and a rigid scope used as a laparoscope and the like. The insertion section 200 is also referred to as a scope. The control device 300 is also referred to as a body section or a processing device. The display section 400 is also referred to as a display device. The external I/F section 500 is also referred to as an operation section or an operation device. The light source device 100 is also referred to as an illumination section or an illumination device.

The light source device 100 generates illumination light. The light source device 100 includes light sources LDV, LDB, LDG, LDA, and LDR, and a multiplexing section 120. Note that the light source device 100 may not include the light source LDA in a first embodiment given below.

Each of the light sources LDV, LDB, LDG, LDA, and LDR is a light emitting diode (LED) or a laser light source. Hereinafter, light generated by the light sources LDV, LDB, LDG, LDA, and LDR is referred to as V light, B light, G light, A light, and R light, respectively.

The V light is narrowband light having a peak wavelength at 410 nm. The V light has a half-value width of several nanometers to several tens of nanometers. The wavelength band of the V light corresponds to a blue wavelength band of white light and is narrower than the blue wavelength band. The B light has the blue wavelength band of white light. The G light has a green wavelength band of white light. The A light is narrowband light having a peak wavelength at 600 nm. The A light has a half-value width of several nanometers to several tens of nanometers. The wavelength band of the A light corresponds to a red wavelength band of white light and is narrower than the red wavelength band. The R light has the red wavelength band of white light. In the case where an image sensor 240 is a Bayer image sensor, the V light and the B light pass through a blue color filter, the G light passes through a green color filter, and the A light and the R light pass through a red color filter.

It should be noted that the above wavelengths are merely exemplary. In an alternative embodiment, the peak wavelength of each light may shift by about 10%, for example. Also, each of the B light, the G light, and the R light may be narrowband light having a half-value width of several nanometers to several tens of nanometers. Also, the light source LDA may emit infrared light instead of the A light.

The multiplexing section 120 multiplexes light emitted by the light sources LDV, LDB, LDG, LDA, and LDR and makes the multiplexed light incident into a light guide 210. For example, the multiplexing section 120 is composed of dichroic mirrors, lenses and the like.

At one light emission timing, the light source device 100 emits light including one or more wavelengths out of the V light, the B light, the G light, the A light, and the R light. Hereinafter, this light including one or more wavelengths emitted at one light emission timing is referred to as an illumination light group. Details of the illumination light will be given later.

The insertion section 200 is a portion inserted into a subject's body. The insertion section 200 includes the light guide 210, an illumination lens 220, an objective lens 230, the image sensor 240, and an A/D conversion circuit 250. The insertion section 200 may also include a memory 260. The insertion section 200 includes a connector (not shown) by which the insertion section 200 is attached to and removed from the control device 300.

The light guide 210 guides illumination light emitted from the light source device 100 to a distal end of the insertion section 200. The illumination lens 220 illuminates an object with the illumination light guided by the light guide 210. In some exemplary embodiments, the object is a tissue. Reflected light from the object is made incident on the objective lens 230. The objective lens 230 forms an object image, which is captured by the image sensor 240.

The image sensor 240 includes a plurality of pixels that photoelectrically converts the object image, and obtains pixel signals from the plurality of pixels. The image sensor 240 is a color image sensor that can obtain pixel signals of a plurality of colors in a single imaging operation. For example, the image sensor 240 is a Bayer image sensor having Bayer array color filters or a complementary color image sensor having complementary color filters.

The A/D conversion circuit 250 performs A/D conversion of analog pixel signals output from the image sensor 240 into digital pixel signals. The A/D conversion circuit 250 may be built into the image sensor 240.

The control device 300 performs signal processing including image processing. The control device 300 also controls each section of the endoscope apparatus. The control device 300 includes a processing circuit 310 and a control circuit 320.

The control circuit 320 controls each section of the endoscope apparatus. For example, a user operates the external I/F section 500 to set whether to enable or disable a highlighting process. For example, in response to input of an instruction to enable a highlighting process, the control circuit 320 outputs an instruction to enable the highlighting process to the processing circuit 310. The processing circuit 310 highlights a blood vessel structure in a white light image based on images such as one obtained with the V light, for example. In response to input of an instruction to disable a highlighting process, the control circuit 320 outputs an instruction to disable the highlighting process to the processing circuit 310. The processing circuit 310 outputs a white light image to the display section 400 without highlighting it.

The memory 260 of the insertion section 200 stores information about the insertion section 200. The control circuit 320 controls each section of the endoscope apparatus based on information read from the memory 260. For example, the memory 260 stores information about the image sensor 240. The information about the image sensor 240 includes information about the kind of the image sensor 240, for example. Based on the information about the image sensor 240 read from the memory 260, the control circuit 320 causes the processing circuit 310 to execute image processing corresponding to that information.

The processing circuit 310 performs image processing based on pixel signals from the A/D conversion circuit 250 to generate a display image, and output the display image to the display section 400. The display section 400 is, for example, a liquid crystal display device or the like, and displays the display image output from the processing circuit 310.

Figure 2:
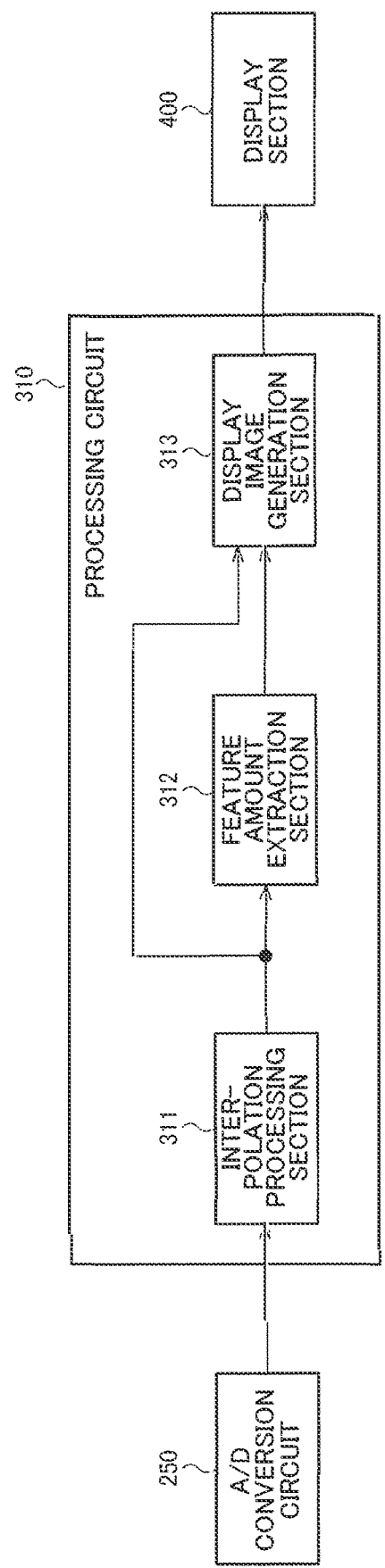
FIG. 2 illustrates a detailed configuration example of a processing circuit.

FIG. 2 illustrates a detailed configuration example of the processing circuit 310. The processing circuit 310 includes an interpolation processing section 311, a feature amount extraction section 312, and a display image generation section 313.

The interpolation processing section 311 receives input of image signals from the A/D conversion circuit 250. Based on the image signals, the interpolation processing section 311 acquires images respectively corresponding to the V light, the B light, the G light, the A light, and the R light. Hereinafter, the images corresponding to the V light, the B light, the G light, the A light, and the R light are respectively referred to as a V image, a B image, a G image, an A image, and an R image. For example, in the case where the image sensor 240 is a Bayer image sensor, an image of the V light is captured by blue pixels. The interpolation processing section 311 interpolates pixel signals of blue pixels to generate the V image. Likewise, images of the B light, the G light, the A light, and the R light are respectively captured by blue pixels, green pixels, red pixels, and red pixels. The interpolation processing section 311 interpolates these pixel signals to generate the B image, the G image, the A image, and the R image.

In the case where the image sensor 240 is a complementary color image sensor and performs interlaced imaging, the interpolation processing section 311 obtains YCrCb signals using the following expressions (1)-(3). The interpolation processing section 311 converts the YCrCb signals into RGB signals. For example, when the V light is emitted, a B channel of the RGB signals corresponds to the V image. Likewise, the interpolation processing section 311 obtains the B image, the G image, the A image, and the R image.

$$Y=\{(Mg+Cy)+(G+Ye)\}/2 \quad (1)$$

$$Cb=(Mg+Cy)-(G+Ye) \quad (2)$$

$$Cr=(Mg+Ye)-(G+Cy) \quad (3)$$

In the above expressions (1)-(3), Mg, Cy, G, and Ye represent pixel values of magenta, cyan, green, and yellow, respectively. Also, (Mg+Cy) represents addition readout of pixel values of magenta and cyan. The Cb signal in the above expression (2) is obtained in one of two fields in the interlaced imaging, and the Cr signal in the above expression (3) is obtained in the other of the two fields.

The display image generation section 313 combines the B image, the G image, and the R image to generate a white light image. The display image generation section 313 also highlights the white light image. Specifically, the feature amount extraction section 312 extracts a feature amount from the V image or the A image. The display image generation section 313 highlights the white light image based on the extracted feature amount. The feature amount extraction section 312 extracts a high-frequency component from the V image to extract a feature amount that indicates a structure of superficial blood vessels. Alternatively, the feature amount extraction section 312 extracts a high-frequency component from the A image to extract a feature amount that indicates a structure of deep blood vessels. The display image generation section 313 adds the high-frequency component extracted by the feature amount extraction section 312 to a G channel for the white light image to thereby highlight the white light image. The display image generation section 313 outputs the highlighted white light image to the display section 400.

The external I/F section 500 is an interface that allows a user to perform an input operation and the like on the endoscope apparatus. In other words, the external I/F section 500 may be an interface for operating the endoscope apparatus, an interface for making operational setting for the endoscope apparatus, or a like interface. For example, the external I/F section 500 includes buttons, dials, levers and the like for operating the endoscope apparatus.

Figure 3:
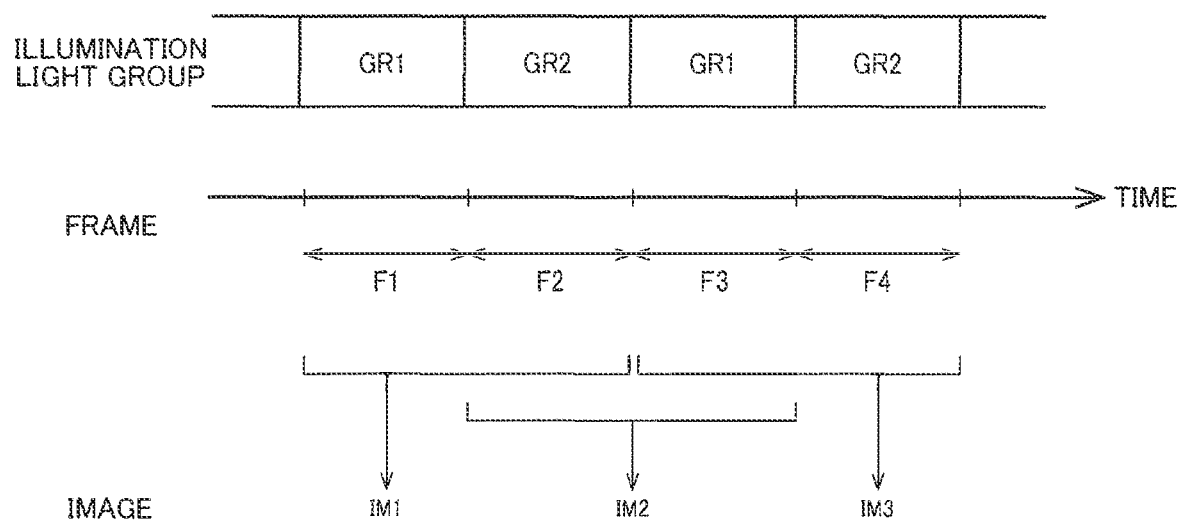
FIG. 3 explains frame sequential imaging performed by the endoscope apparatus of some exemplary embodiments.

FIG. 3 explains frame sequential imaging performed by the endoscope apparatus of the exemplary embodiments. As shown in FIG. 3, the light source device 100 emits a first illumination light group GR1 in a first frame F1, emits a second illumination light group GR2 in a second frame F2, emits the first illumination light group GR1 in a third frame F3, and emits the second illumination light group GR2 in a fourth frame F4. Each frame is a period in which the image sensor 240 captures an image, corresponding to a frame in video imaging. In the case of interlaced imaging by a complementary color image sensor, two fields correspond to one frame.

The image sensor 240 captures images of an object irradiated with the first illumination light group GR1 in the first and third frames F1, F3, and captures images of the object irradiated with the second illumination light group GR2 in the second and fourth frames F2, F4.

The processing circuit 310 generates a first display image IM1 based on the images captured in the first and second frames F1, F2. Also, the processing circuit 310 generates a second display image IM2 based on the images captured in the second and third frames F2, F3, and generates a third display image IM3 based on the images captured in the third and fourth frames F3, F4. The display images IM1-IM3 serve as frame images in a video. Similar operations follow to make a video, which is displayed by the display section 400.

Below a description will be given of operations and processing of the endoscope apparatus of the exemplary embodiments, with reference to particular embodiments given later as needed.

The endoscope apparatus of the exemplary embodiments includes the light source device 100, the image sensor 240, and the processing circuit 310. As has been explained in FIG. 3, the light source device 100 alternately emits the first illumination light group GR1 and the second illumination light group GR2. As explained in FIGS. 4 and 5, the first illumination light group GR1 includes the G light with a green wavelength band, whereas the second illumination light group GR2 does not include the G light. The image sensor 240 includes color filters of a plurality of colors. As has been explained in FIG. 3, the processing circuit 310 generates a display image based on the image captured by the image sensor 240 with the first illumination light group GR1 emitted and the image captured by the image sensor 240 with the second illumination light group GR2 emitted. The first illumination light group GR1 includes the V light corresponding to a narrowband in the blue wavelength band. The processing circuit 310 generates a G channel image in the display image based on the G image obtained with the G light and the V image obtained with the V light.

In the exemplary embodiments, the image sensor 240 includes the color filters of a plurality of colors, and the light source device 100 alternately emits the first illumination light group GR1 and the second illumination light group GR2. This means that light emission for frame sequential imaging is performed only twice, which reduces color deviation. In the exemplary embodiments, the light source device 100 simultaneously emits the G light and the V light, and the processing circuit 310 highlights the G channel of the display image using the V image. As the highlighting is performed using the images captured at the same timing, this highlighting process can produce a high-quality highlighted image. In the exemplary embodiments, the light source device 100 alternately emits the first illumination light group GR1 which includes the G light with the green wavelength band, and the second illumination light group GR2 which does not include the G light. An image of a structure that can be captured with the G light is captured only when the first illumination light group GR1 is emitted, and is not captured when the second illumination light group GR2 is emitted. This means that color mixture due to the G light does not occur when the second illumination light group GR2 is emitted. This reduces the possibility of flicker, a phenomenon in which an object looks flickering.

The G light is also referred to as green light, and the V light is also referred to as blue narrowband light. The G image is also referred to as a green image, and the V image is also referred to as a blue narrowband image. The G channel is also referred to as a green channel.

Figure 4:
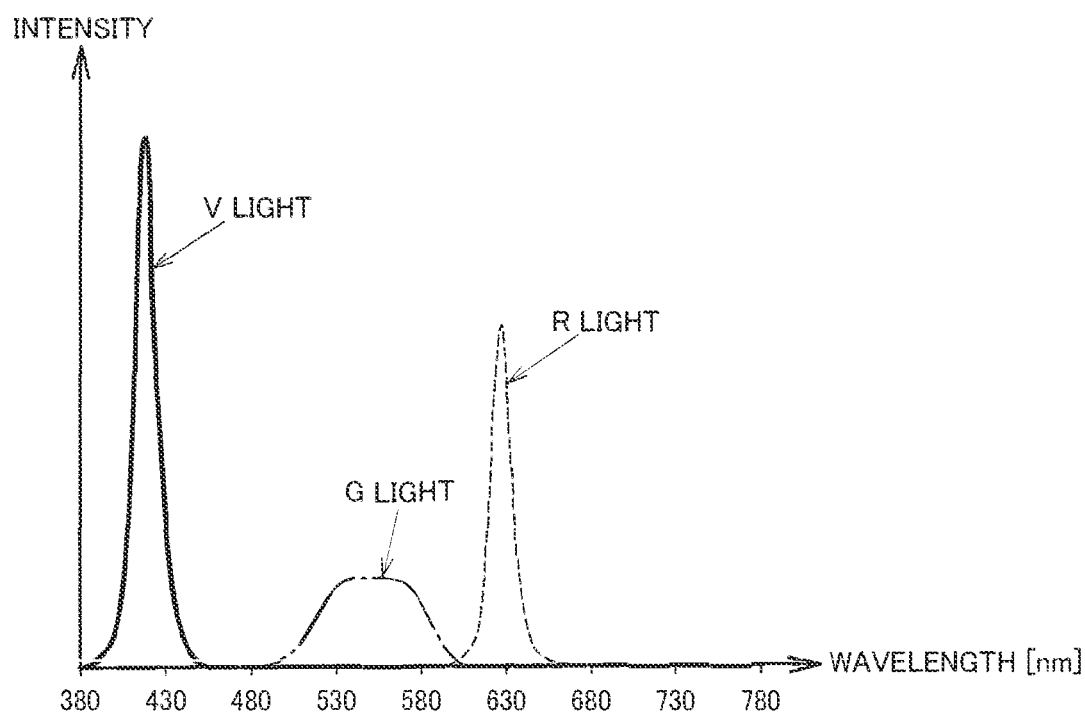
FIG. 4 illustrates a spectrum of illumination light in accordance with a first embodiment.
Figure 5:
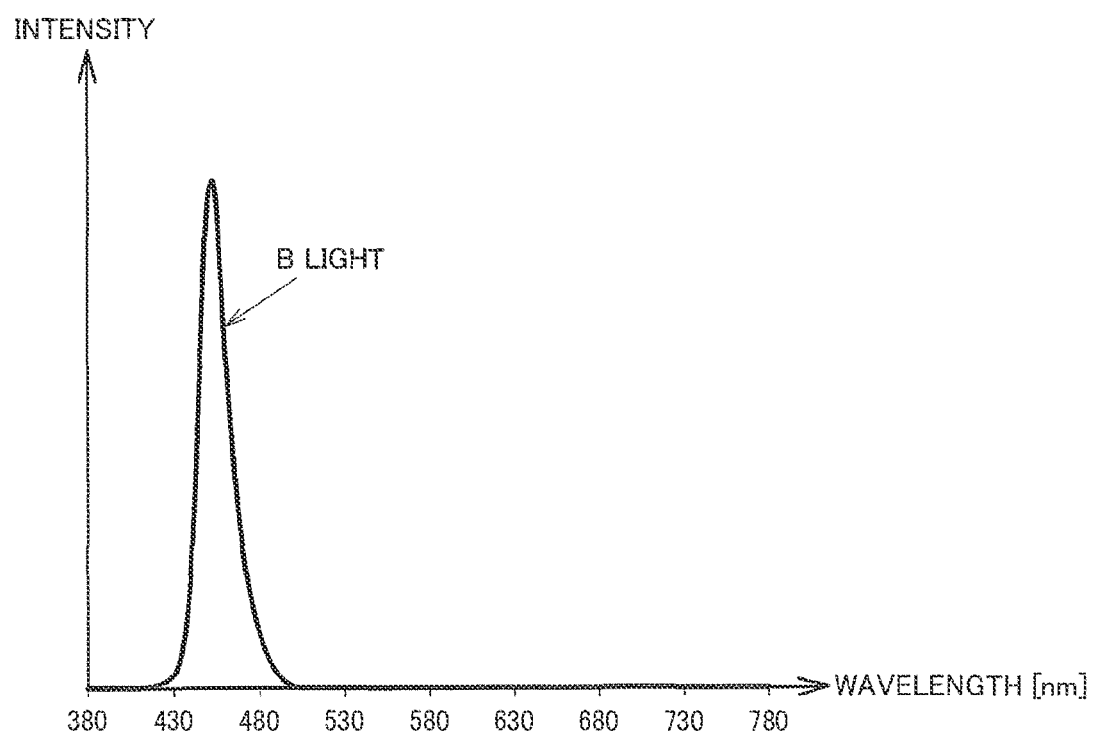
FIG. 5 illustrates a spectrum of illumination light in accordance with the first embodiment.

As explained in FIGS. 4 and 5 in particular, the first illumination light group GR1 includes the R light with the red wavelength band. The second illumination light group GR2 includes the B light with the blue wavelength band.

In the exemplary embodiments, the V, G, and R images can be captured with the first illumination light group GR1 emitted. The B image can be captured with the second illumination light group GR2 emitted. This allows a display image to be generated based on the V, B, G, and R images. At this time, the G channel of the display image is generated based on the V image and the G image, as described above.

In the exemplary embodiments, the processing circuit 310 generates a white light image as the display image based on the R image obtained with the R light, the G image, and the B image obtained with the B light. Based on the V image, the processing circuit 310 performs a structure highlighting process on the G channel image.

Since the G light for capturing the G image and the V light for capturing the V image are simultaneously emitted, the V image and the G channel image constitute an image of the object at the same timing. This allows for obtaining a high-quality highlighted image from the structure highlighting process on the G channel image based on the V image. In other words, this structure highlighting process can reduce problems such as misalignment of edges.

As has been described in FIG. 3, the light source device 100 emits the first illumination light group GR1 in the first frame F1, emits the second illumination light group GR2 in the second frame F2, emits the first illumination light group GR1 in the third frame F3, and emits the second illumination light group GR2 in the fourth frame F4. The processing circuit 310 generates the first display image IM1 based on the image captured by the image sensor 240 in the first frame F1 and the image captured by the image sensor 240 in the second frame F2. The processing circuit 310 generates the second display image IM2 based on the image captured by the image sensor 240 in the second frame F2 and the image captured by the image sensor 240 in the third frame F3. The processing circuit 310 generates the third display image IM3 based on the image captured by the image sensor 240 in the third frame F3 and the image captured by the image sensor 240 in the fourth frame F4.

The exemplary embodiments enable two-frame sequential imaging using the color image sensor. As the first illumination light group GR1 including the G light is emitted once every two frames, the G image is updated once every two frames. Specifically, the second display image IM2 and the third display image IM3 have the G image in common. Here, the B image combined with the G image in the second display image IM2 and the B image combined with the G image in the third display image IM3 are captured at different timings. Nonetheless, no color mixture occurs because the light source device 100 does not emit the G light when taking the B image. This reduces flicker.

Figure 7:
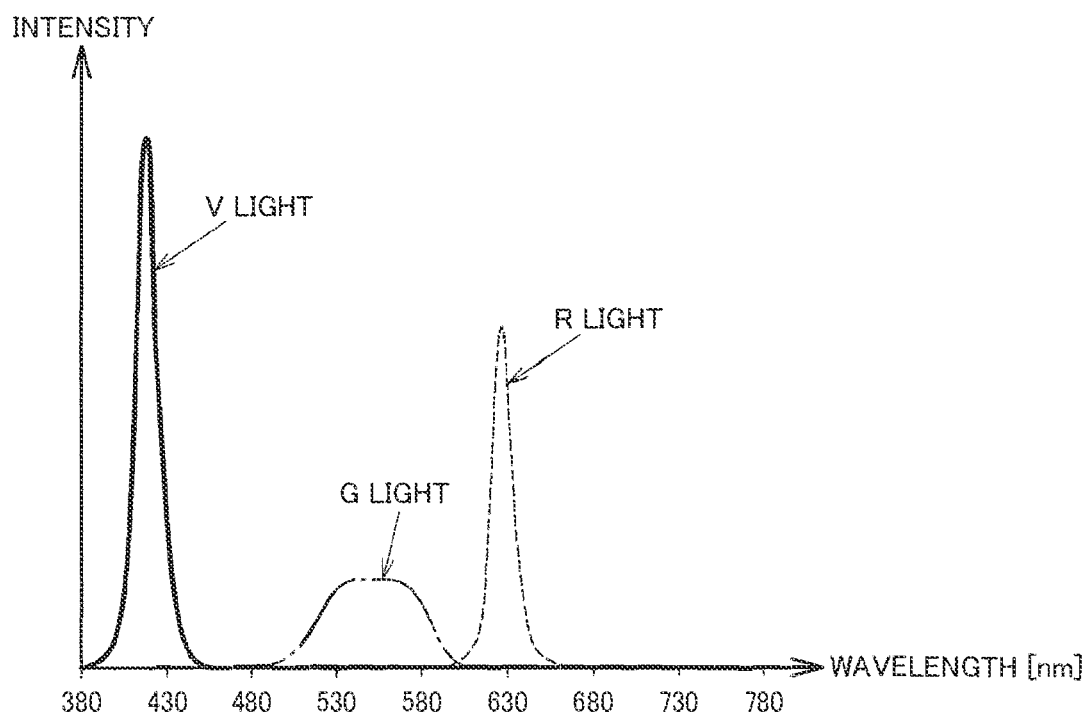
FIG. 7 illustrates a spectrum of illumination light in accordance with a second embodiment.
Figure 8:
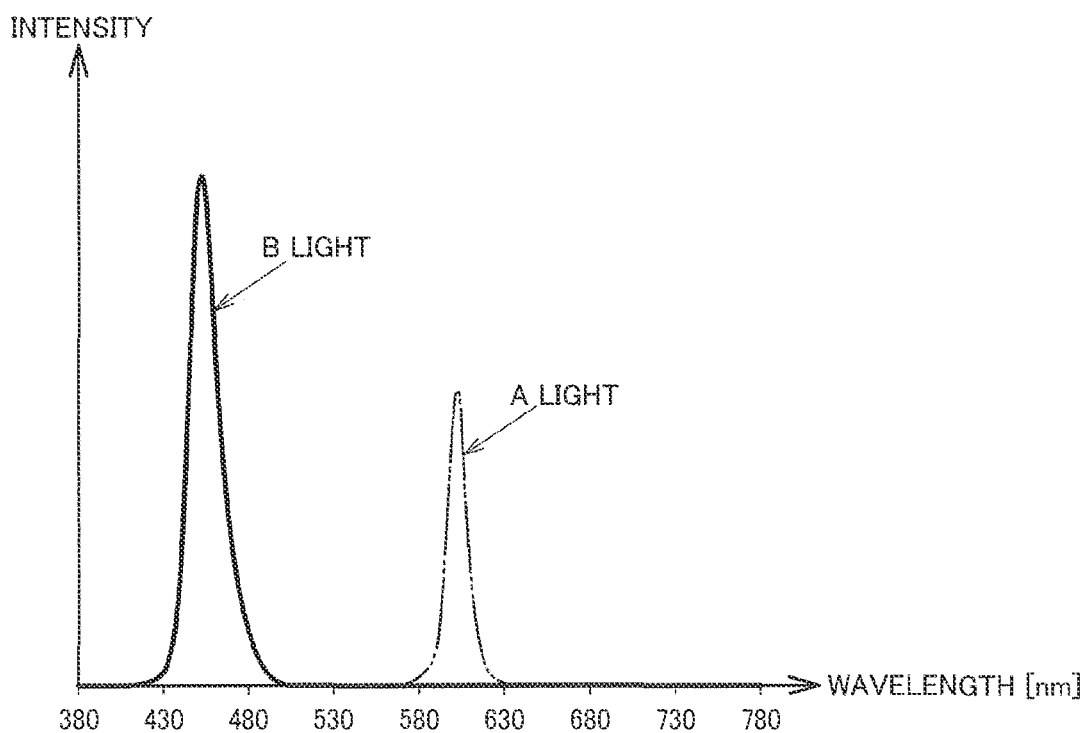
FIG. 8 illustrates a spectrum of illumination light in accordance with the second embodiment.

As explained in FIGS. 7 and 8, in a second embodiment, the second illumination light group GR2 includes the A light. As explained in FIG. 9, the processing circuit 310 generates the G channel image in the display image based on the G image, the V image, and the A image obtained with the A light. The A light is also referred to as red narrowband light, and the A image is also referred to as a red narrowband image.

The A light has a longer wavelength than the V light and thus reaches deeper into a mucosa than the V light does. Thus, the use of the A light enables image capturing of deep blood vessels. The exemplary embodiments enable highlighting of blood vessels in a mucosal deep layer by a highlighting process on the display image based on the A image as well as highlighting of blood vessels in a mucosal surface layer by the highlighting process on the display image based on the V image.

In the exemplary embodiments, the V light has a peak wavelength at 415 nm±20 nm.

Hemoglobin has the largest absorbance at 415 nm±20 nm. This means that the V light having a peak wavelength at 415 nm±20 nm is easily absorbed by hemoglobin. The use of the V light enables image capturing of a region with a high hemoglobin concentration, such as blood vessels in the mucosa. The V light scatters in a relatively shallow portion of the mucosa, and thus enables image capturing of blood vessels in a mucosal surface layer.

In the exemplary embodiments, the A light has a peak wavelength at 600 nm±20 nm.

Near 600 nm, the absorption coefficient of hemoglobin decreases in proportion to an increase in wavelength. Nonetheless, the absorption coefficient of hemoglobin is still large enough at 600 nm±20 nm. Hence, the use of the A light enables image capturing of a region with a high hemoglobin concentration, such as blood vessels in the mucosa. The A light has a longer wavelength than the V light, and thus can reach relatively deep into the mucosa. In other words, the use of the A light enables image capturing of blood vessels in a mucosal deep layer.

Figure 6:
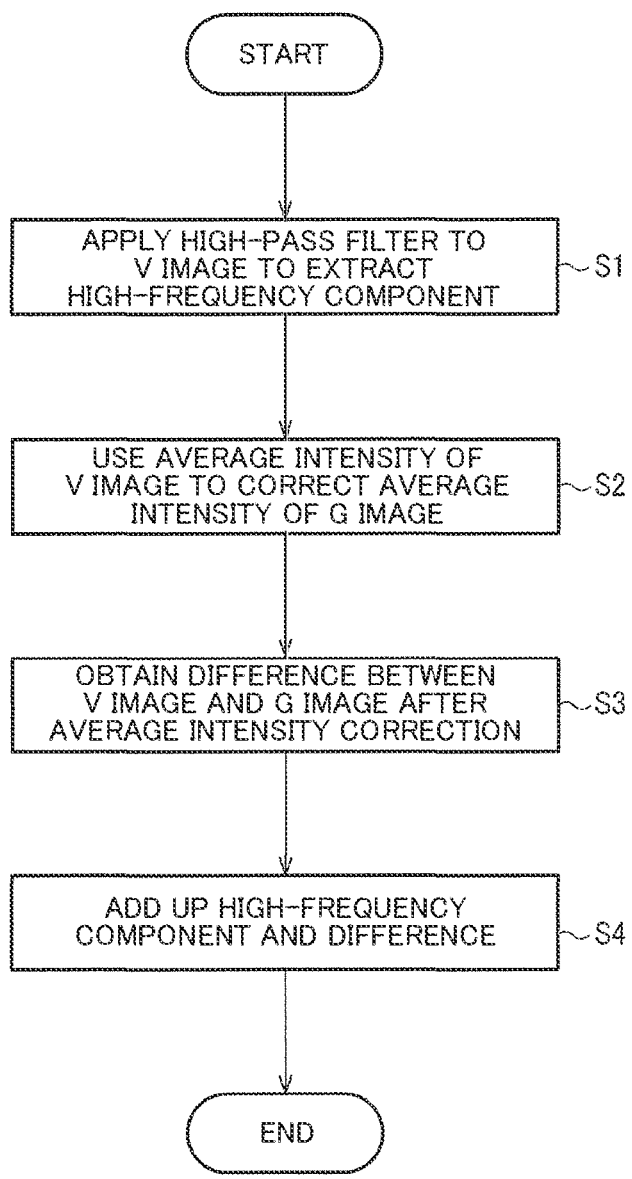
FIG. 6 is a flowchart of processing performed by a feature amount extraction section in accordance with the first embodiment.

As explained in FIG. 6, the processing circuit 310 extracts a feature amount associated with a structure of the object based on the G image and the V image. The feature amount takes a larger value at a position where a structure of interest is present. The feature amount is an edge component, for example. Specifically, the processing circuit 310 applies a high-pass filter to the V image to extract an edge component. Also, the processing circuit 310 obtains a difference between the G image and the V image to extract a structure that is not captured in the G image but is captured in the V image. In other words, based on a correlation between the G image and the V image, the processing circuit 310 extracts a structure that is not captured in the G image but is captured in the V image. The processing circuit 310 highlights the display image based on this correlation.

In the exemplary embodiments, the processing circuit 310 combines the above feature amount into the G image to highlight a structure of the object in the display image.

As described above, the V image captures blood vessels in a mucosal surface layer. Thus, a feature amount extracted from the V image is associated with the blood vessels in the mucosal surface layer. Combining this feature amount into the G image enables highlighting of a blood vessel structure in the display image.

The processing circuit 310 may extract a feature amount associated with a structure of the object based on the G image and the A image. The feature amount takes a larger value at a position where a structure of interest is present. The feature amount is an edge component, for example. Specifically, the processing circuit 310 may apply a high-pass filter to the A image to extract an edge component. Also, the processing circuit 310 may obtain a difference between the G image and the A image to extract a structure that is not captured in the G image but is captured in the A image. In other words, based on a correlation between the G image and the A image, the processing circuit 310 extracts a structure that is not captured in the G image but is captured in the A image. The processing circuit 310 may highlight the display image based on this correlation. The processing circuit 310 may combine the above feature amount into the G image to highlight a structure of the object in the display image.

As described above, the A image captures blood vessels in a mucosal deep layer. Thus, a feature amount extracted from the A image is associated with the blood vessels in the mucosal deep layer. Combining this feature amount into the G image enables highlighting of a blood vessel structure in the display image.

The above description has been given of the case where the light source device 100 simultaneously emits the G light and the V light, but this is by way of example only and the light source device 100 may simultaneously emit the G light and the A light. In other words, the first illumination light group GR1 may include the A light corresponding to a narrowband in the red wavelength band. The processing circuit 310 may generate the G channel image in the display image based on the G image and the A image obtained with the A light. Specifically, the first illumination light group GR1 may include the G light and the A light, and the second illumination light group GR2 may include the B light and the R light. The first illumination light group GR1 may further include the V light.

This configuration allows the G image and the A image to be simultaneously captured, providing advantageous effects similar to those resulting from simultaneously capturing the G image and the V image. Specifically, this configuration can reduce color deviation as the light emission for frame sequential imaging is performed only twice. Besides, the highlighting process using the images captured at the same timing can produce a high-quality highlighted image. Additionally, alternating emission of the first illumination light group GR1 and the second illumination light group GR2, where the first illumination light group GR1 includes the G light with the green wavelength band and the second illumination light group GR2 does not include the G light, can reduce the possibility of flicker.

The above description has been given of the case where the G image is input to the G channel of the display image, but this is by way of example only and an image captured by illumination light other than the G light may be input to the G channel. For example, in narrow band imaging (NBI), the B image is input to the G channel of the display image. The present disclosure may be applied to such cases.

Specifically, the light source device 100 alternately emits a first illumination light group including first color light with a wavelength band of a first color and a second illumination light group not including the first color light. The image sensor 240 includes color filters of a plurality of colors. The processing circuit 310 generates a display image based on an image captured by the image sensor with the first illumination light group emitted and an image captured by the image sensor with the second illumination light group emitted. The first illumination light group includes second color narrowband light corresponding to a narrowband in a wavelength band of a second color. The processing circuit 310 generates a G channel image in the display image based on a first color image obtained with the first color light and a second color narrowband image obtained with the second color narrowband light.

For example, in the case where the first color is blue, the second color is one of green and red, and a third color is the other of green and red. The second illumination light group includes at least one of second color light and third color light. For example, the processing circuit 310 inputs the first color image to the G channel of the display image, and performs a structure highlighting process on the G channel of the display image based on the second color narrowband image.

The control device 300 of the exemplary embodiments may be configured as follows. Specifically, each of the processing circuit 310 and the control circuit 320 is configured with the following hardware. The processing circuit 310 and the control circuit 320 may also be integrally configured with the following hardware. The hardware may include at least one of a digital signal processing circuit and an analog signal processing circuit. For example, the hardware may be composed of one or more circuit devices mounted on a circuit board or may be composed of one or more circuit elements. The one or more circuit devices is an integrated circuit (IC), for example. The one or more circuit elements is a resistor or a capacitor, for example.

Alternatively, the processing circuit 310 and the control circuit 320 may be individually implemented by the following processor. The processing circuit 310 and the control circuit 320 may also be implemented by a single processor. That is, the control device 300 of the exemplary embodiments may include a memory storing information and a processor configured to operate based on the information stored in the memory. The information may include programs and various data, for example. The processor may include hardware. The processor controls the light source device 100 to alternately emit the first illumination light group GR1 and the second illumination light group GR2. The processor generates the display image based on the image captured by the image sensor 240 with the first illumination light group GR1 emitted and the image captured by the image sensor 240 with the second illumination light group GR2 emitted. At this time, the processor generates the G channel image in the display image based on the G image and the V image.

The processor may also be a central processing unit (CPU), for example. The processor is, however, not limited to the CPU and may be any of various processors including a graphics processing unit (GPU) and a digital signal processor (DSP). The memory may be a semiconductor memory such as a static random-access memory (SRAM) and a dynamic random-access memory (DRAM) or may be a register. The memory may also be a magnetic storage device such as a hard disk device, or may be an optical storage device such as an optical disk device. For example, the memory stores computer-readable instructions, and the processor executes the instructions to implement functions of the respective sections in the control device 300 as the processes. These instructions may be an instruction set included in a program or may be instructions that cause operations of the hardware circuit included in the processor.

For example, the processor implements the functions of the processing circuit 310 in FIG. 1. Alternatively, the processor implements the functions of both of the processing circuit 310 and the control circuit 320 in FIG. 1.

Each section of the endoscope apparatus of the exemplary embodiments may be implemented as modules of a program running on the processor. For example, the program includes a light source control module and a processing module; the light source control module is configured to control the light source device 100 to alternately emit the first illumination light group GR1 and the second illumination light group GR2, and the processing module is configured to generate the display image based on the image captured by the image sensor 240 with the first illumination light group GR1 emitted and the image captured by the image sensor 240 with the second illumination light group GR2 emitted. The processing module is configured to generate the G channel image in the display image based on the G image and the V image.

The program for implementing the processes performed by the respective sections in the control device 300 of the exemplary embodiments may be, for example, stored in an information storage medium that is a computer-readable medium. For example, the information storage medium may be implemented as an optical disk, a memory card, a hard disk drive (HDD), or a semiconductor memory. The semiconductor memory is a read-only memory (ROM), for example. The processing circuit 310 and the control circuit 320 perform various processes in the exemplary embodiments based on the program and data stored in the information storage medium. In other words, the information storage medium stores the program for causing a computer to function as each section of the endoscope apparatus of the exemplary embodiments. The computer is a device including an input device, a processing section, a storage section, and an output section. The program causes the computer to execute the processing in each section. The program is stored in the information storage medium. Examples of the information storage medium may include various storage media that are readable by an optical detection system, such as an optical disk (e.g., DVD and CD), a magneto-optical disk, a hard disk, and a memory (e.g., nonvolatile memory and RAM).

2. First Embodiment

FIGS. 4 and 5 illustrate spectra of the illumination light in accordance with the first embodiment; FIG. 4 illustrates a spectrum of the light included in the first illumination light group, and FIG. 5 illustrates a spectrum of the light included in the second illumination light group.

In the first embodiment, the light source device 100 emits the V light, the G light, and the R light as the first illumination light group GR1 in FIG. 3, and emits the B light as the second illumination light group GR2 in FIG. 3.

In the frames F1, F3, in which the first illumination light group GR1 is emitted, the interpolation processing section 311 generates an RGB image by interpolation processing and outputs a B channel of the RGB image as the V image, a G channel of the RGB image as the G image, and an R channel of the RGB image as the R image.

In the frames F2, F4, in which the second illumination light group GR2 is emitted, the interpolation processing section 311 generates a B channel of an RGB image by interpolation processing and outputs the B channel as the B image. The interpolation processing section 311 does not generate the G channel and the R channel, or generates the G channel and the R channel but does not output them.

FIG. 6 is a flowchart of processing performed by the feature amount extraction section 312 in accordance with the first embodiment.

At step S1, the feature amount extraction section 312 applies a high-pass filter to the V image to extract a high-frequency component of the V image.

At step S2, the feature amount extraction section 312 obtains an average intensity of the V image. The average intensity represents an average value of pixel values, for example. The average intensity may be an average value over the entire image or an average value in each local region in the image. The feature amount extraction section 312 corrects an average intensity of the G image based on the average intensity of the V image. For example, the feature amount extraction section 312 corrects the average intensity of the G image such that the average intensity of the V image and the average intensity of the G image are the same as each other or such that the average intensity of the V image and the average intensity of the G image are in a predetermined ratio to each other.

At step S3, the feature amount extraction section 312 obtains a difference between the V image and the G image whose average intensity has been corrected.

At step S4, the feature amount extraction section 312 adds up the high-frequency component obtained at step S1 and the difference obtained at step S3.

The display image generation section 313 combines the R, G, and B images output from the interpolation processing section 311 to generate a white light image. The display image generation section 313 adds the added-up value obtained by the feature amount extraction section 312 at step S4 to the G channel of the white light image to thereby highlight the white light image.

In the wavelengths of the V light, hemoglobin has a high absorption coefficient, and also has a high scattering coefficient in a mucosa relative to the scattering coefficient in the other wavelengths of visible light. For this reason, the V image captures blood vessels in a mucosal surface layer in high contrast. Thus, the above highlighting process allows the blood vessel structure in the mucosal surface layer to be highlighted within the white light image.

In the aforementioned first embodiment, the image sensor 240 is a color image sensor, and the light source device 100 divides the four light sources into two groups and causes the two groups to alternately emit light. Hence, light emission for frame sequential imaging is performed only twice, which is fewer than in the case of four-frame sequential imaging using a monochrome image sensor. More frequent light emission for frame sequential imaging increases a difference in imaging timings between colors, which increases the likelihood of color deviation. In this regard, the present embodiment requires the light emission for frame sequential imaging to be performed only twice, reducing color deviation.

In the present embodiment, the light source device 100 simultaneously emits the G light and the V light in the frames F1, F3, and the processing circuit 310 inputs the G image to the G channel of the display image and highlights the G channel of the display image using the V image. If the V image and the G image are captured at different timings, image quality of the highlighted G channel may be degraded (for example, an edge may look doubled). In the three primary colors, green has a higher contribution to luminance and thus has a large influence on degradation in image quality. In this regard, the present embodiment captures the V image and the G image at the same timing, and can thereby produce a high-quality highlighted image.

In the present embodiment, the light source device 100 emits the G light in the frames F1, F3 and does not emit the G light in the frames F2, F4. That is, the G light is emitted only at one of the two alternately repeated emission timings. This reduces degradation in image quality caused by color mixture or flicker. Assume that the G light is emitted also in the frames F2, F4. Then, the B image would be sensitive to the G light due to sensitivity characteristics of the color filters of the image sensor 240. In other words, an object image captured by the G light would mix with the B image. Such color mixture might degrade the quality of the display image. Additionally, the object image captured by the G light and mixed with the B image is captured at a timing different from a timing of capturing the G image. This difference in timings might cause flicker. The present embodiment can reduce degradation in image quality due to color mixture or flicker by not emitting the G light in the frames F2, F4.

3. Second Embodiment

FIGS. 7 and 8 illustrate spectra of the illumination light in accordance with the second embodiment; FIG. 7 illustrates a spectrum of the light included in the first illumination light group, and FIG. 8 illustrates a spectrum of the light included in the second illumination light group.

In the second embodiment, the light source device 100 emits the V light, the G light, and the R light as the first illumination light group GR1 in FIG. 3, and emits the B light and the A light as the second illumination light group GR2 in FIG. 3.

In the frames F1, F3, in which the first illumination light group GR1 is emitted, the interpolation processing section 311 generates an RGB image by interpolation processing and outputs a B channel of the RGB image as the V image, a G channel of the RGB image as the G image, and an R channel of the RGB image as the R image.

In the frames F2, F4, in which the second illumination light group GR2 is emitted, the interpolation processing section 311 generates a B channel and an R channel of an RGB image by interpolation processing and outputs the B channel as the B image and the R channel as the A image. The interpolation processing section 311 does not generate the G channel, or generates the G channel but does not output it.

Figure 9:
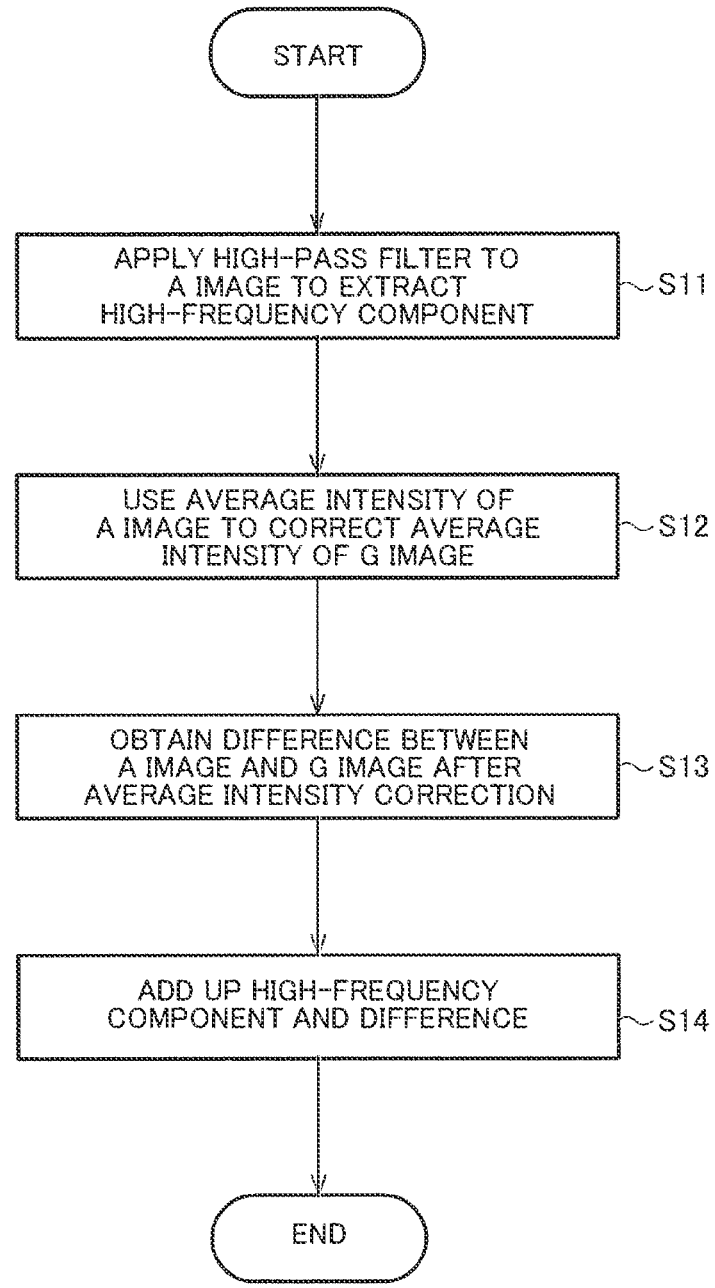
FIG. 9 is a flowchart of processing performed by the feature amount extraction section in accordance with the second embodiment.

FIG. 9 is a flowchart of processing performed by the feature amount extraction section 312 in the second embodiment. In the second embodiment, the feature amount extraction section 312 also executes the process flow shown in FIG. 6. The feature amount extraction section 312 may execute the process flows in FIGS. 6 and 9 in any order.

At step S11, the feature amount extraction section 312 applies a high-pass filter to the A image to extract a high-frequency component of the A image. A cutoff frequency of the high-pass filter used at step S11 may differ from that of the high-pass filter used at step S1 in FIG. 6.

At step S12, the feature amount extraction section 312 obtains an average intensity of the A image. The average intensity represents an average value of pixel values, for example. The average intensity may be an average value over the entire image or an average value in each local region in the image. The feature amount extraction section 312 corrects an average intensity of the G image based on the average intensity of the A image. For example, the feature amount extraction section 312 corrects the average intensity of the G image such that the average intensity of the A image and the average intensity of the G image are the same as each other or such that the average intensity of the A image and the average intensity of the G image are in a predetermined ratio to each other.

At step S13, the feature amount extraction section 312 obtains a difference between the A image and the G image whose average intensity has been corrected.

At step S14, the feature amount extraction section 312 adds up the high-frequency component obtained at step S11 and the difference obtained at step S13.

The display image generation section 313 combines the R, G, and B images output from the interpolation processing section 311 to generate a white light image. The display image generation section 313 adds the added-up values obtained by the feature amount extraction section 312 at step S4 in FIG. 6 and step S14 in FIG. 9 to the G channel of the white light image to thereby highlight the white light image.

As has been described in the first embodiment, the V image captures blood vessels in a mucosal surface layer in high contrast. Further, in the wavelengths of the A light, hemoglobin has a certain degree of absorption coefficient as compared to the absorption coefficient in the wavelengths of the R light, and also has a low scattering coefficient in a mucosa relative to the scattering coefficient in the other wavelengths of visible light. For this reason, the A image captures blood vessels in a mucosal deep layer in high contrast. Thus, the above highlighting process allows the blood vessel structures in the mucosal surface layer and the mucosal deep layer to be highlighted within the white light image.

Similarly to the first embodiment, the aforementioned second embodiment can reduce color deviation as the light emission for frame sequential imaging is performed only twice. Additionally, the processing circuit 310 of the second embodiment highlights the G channel of the display image using the A image. In this regard, the second embodiment captures the A image and the G image at the same timing and can thereby produce a high-quality highlighted image. Further, similarly to the first embodiment, the second embodiment can also reduce degradation in image quality due to color mixture or flicker by not emitting the G light in the frames F2, F4.

4. Feature Amount Extraction Section

Figure 10:
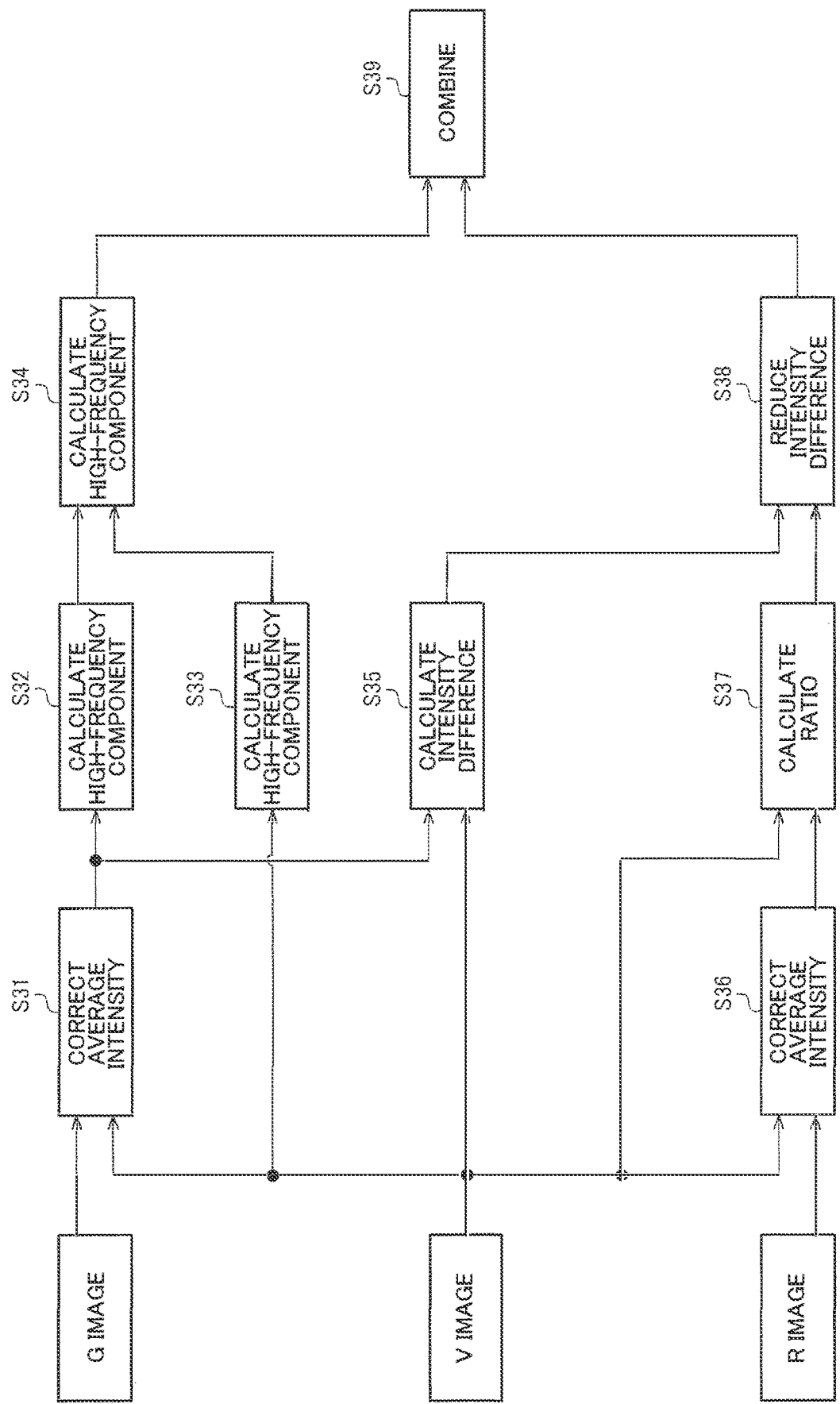
FIG. 10 is a flowchart of detailed processing performed by the feature amount extraction section.

FIG. 10 is a flowchart of detailed processing performed by the feature amount extraction section 312. The process flow of FIG. 10 is applicable to both of the first and second embodiments.

At step S31, the feature amount extraction section 312 obtains an average intensity of the V image, and corrects an average intensity of the G image based on the average intensity of the V image. Through this correction, the feature amount extraction section 312 matches average brightness of the G image with average brightness of the V image.

At step S32, the feature amount extraction section 312 applies a high-pass filter to the G image whose average intensity has been corrected. The feature amount extraction section 312 outputs an output from the high-pass filter as a high-frequency component of the G image.

At step S33, the feature amount extraction section 312 applies a high-pass filter to the V image. The feature amount extraction section 312 outputs an output from the high-pass filter as a high-frequency component of the V image.

At step S34, the feature amount extraction section 312 calculates a difference between the high-frequency component of the V image calculated at step S33 and the high-frequency component of the G image calculated at step S32.

At step S35, the feature amount extraction section 312 calculates a difference between the V image and the G image whose average intensity has been corrected at step S31. This difference is referred to as an intensity difference. The intensity refers to a pixel value in each image. While the intensity difference is used to highlight a white light image, directly using the intensity difference in a highlighting process may result in excessive highlighting of a blood vessel structure. Thus, the feature amount extraction section 312 reduces the intensity difference at steps S36-S38.

At step S36, the feature amount extraction section 312 corrects an average intensity of the R image based on the average intensity of the V image. Through this correction, the feature amount extraction section 312 matches average brightness of the R image with the average brightness of the V image.

At step S37, the feature amount extraction section 312 calculates a ratio between the V image and the R image whose average intensity has been corrected. The ratio represents an intensity ratio between the images and, for example, is calculated for each pixel.

At step S38, the feature amount extraction section 312 reduces the intensity difference calculated at step S35 using the ratio calculated at S37. For example, in the case where the ratio of the intensity of the V image to the intensity of the R image is calculated at step S37, the feature amount extraction section 312 divides the intensity difference by this ratio. The feature amount extraction section 312 carries out this operation for each pixel, for example.

At step S39, the feature amount extraction section 312 combines the difference between the high-frequency components calculated at step S34 and the intensity difference reduced at step S38. This combining is done by adding-up of the differences, for example. The feature amount extraction section 312 carries out this operation for each pixel, for example.

The display image generation section 313 adds the combined value obtained by the feature amount extraction section 312 at step S39 to the G channel of the white light image. The display image generation section 313 carries out this operation for each pixel, for example. The display image generation section 313 thus highlights a blood vessel structure in the white light image based on the V image.

Although the embodiments to which the present disclosure is applied and the modifications thereof have been described in detail above, the present disclosure is not limited to the embodiments and the modifications thereof, and various modifications and variations in components may be made in implementation without departing from the spirit and scope of the present disclosure. The plurality of elements disclosed in the embodiments and the modifications described above may be combined as appropriate to implement the present disclosure in various ways. For example, some of all the elements described in the embodiments and the modifications may be deleted. Furthermore, elements in different embodiments and modifications may be combined as appropriate. Thus, various modifications and applications can be made without departing from the spirit and scope of the present disclosure. Any term cited with a different term having a broader meaning or the same meaning at least once in the specification and the drawings can be replaced by the different term in any place in the specification and the drawings.

What is claimed is:

1. An endoscope apparatus comprising:
a light source configured to:
  in a first frame, emit a first illumination light group;
  in a second frame, emit a second illumination light group; and
  in a third frame, emit the first illumination light group,
  wherein the first illumination light group includes green light with a green wavelength band and first blue light with a first blue wavelength band, and
  wherein the second illumination light group does not include the green light;
an image sensor; and
a processor configured to:
  generate a first display image on the basis of an image captured by the image sensor in the first frame and an image captured by the image sensor in the second frame; and
  generate a second display image on the basis of the image captured by the image sensor in the second frame and an image captured by the image sensor in the third frame.

2. The endoscope apparatus according to claim 1,
wherein the first illumination light group further includes red light with a red wavelength band, and
wherein the second illumination light group includes second blue light with a second blue wavelength band.

3. The endoscope apparatus according to claim 2,
wherein the processor is configured to:
  obtain:
    a red image corresponding to the red light based on the image captured by the image sensor in the first frame;
    a green image corresponding to the green light based on the image captured by the image sensor in the first frame;
    a first blue image corresponding to the first blue light based on the image captured by the image sensor in the first frame; and
    a second blue image corresponding to the second blue light based on the image captured by the image sensor in the second frame;
  generate a white light image based on the red image, the green image and the second blue image;
  generate a green channel image based on the green image and the first blue image; and
  perform a structure highlighting process on the green channel image based on the first blue image.

4. The endoscope apparatus according to claim 1,
wherein the light source is configured to, in a fourth frame, emit the second illumination light group, and
wherein the processor is configured to generate a third display image on the basis of the image captured by the image sensor in the third frame and an image captured by the image sensor in the fourth frame.

5. The endoscope apparatus according to claim 1,
wherein the second illumination light group includes red light with a red wavelength band, and
wherein the processor is configured to:
  obtain:
    a green image corresponding to the green light based on the image captured by the image sensor in the first frame;
    a first blue image corresponding to the first blue light based on the image captured by the image sensor in the first frame; and
    a red image corresponding to the red light based on the image captured by the image sensor in the second frame; and generate a green channel image based on the green image, the first blue image and the red image.

6. The endoscope apparatus according to claim 1, wherein the first blue wavelength band has a peak wavelength at 415 nm±20 nm.

7. The endoscope apparatus according to claim 5, wherein the red wavelength band has a peak wavelength at 600 nm±20 nm.

8. The endoscope apparatus according to in claim 1, wherein the processor is configured to:
obtain:
a green image corresponding to the green light based on the image captured by the image sensor in the first frame; and
a first blue image corresponding to the first blue light based on the image captured by the image sensor in the first frame; and
extract a feature amount associated with a structure of an object, on the basis of the green image and the first blue image.

9. The endoscope apparatus according to claim 8, wherein the processor is configured to combine the feature amount into the green image to highlight the structure of the object in the green image.

10. An endoscope apparatus comprising:
a light source configured to:
in a first frame, emit a first illumination light group;
in a second frame, emit a second illumination light group; and
in a third frame, emit the first illumination light group,
wherein the first illumination light group includes green light with a green wavelength band and first red light with a first red wavelength band, and
wherein the second illumination light group does not include the green light;
an image sensor; and
a processor configured to:
generate a first display image on the basis of an image captured by the image sensor in the first frame and an image captured by the image sensor in the second frame; and
generate a second display image on the basis of the image captured by the image sensor in the second frame and an image captured by the image sensor in the third frame.

11. The endoscope apparatus according to claim 10, wherein the first illumination light further includes blue light with a blue wavelength band, and
wherein the second illumination light group includes second red light with second red wavelength band.

12. The endoscope apparatus according to claim 11, wherein the processor is configured to:
obtain:
a green image corresponding to the green light based on the image captured by the image sensor in the first frame;
a blue image corresponding to the blue light based on the image captured by the image sensor in the first frame; and
a second red image corresponding to the second red light based on the image captured by the image sensor in the second frame;
generate a white light image based on the green image, the blue image and the second red image;
generate a green channel image based on the green image and the blue image; and
perform a structure highlighting process on the green channel image based on the blue image.

13. The endoscope apparatus according to claim 10, wherein the light source is configured to, in a fourth frame, emit the second illumination light group, and
wherein the processor is configured to generate a third display image on the basis of the image captured by the image sensor in the third frame and an image captured by the image sensor in the fourth frame.

14. The endoscope apparatus according to claim 10, wherein the first illumination light group further includes a first blue light with a first blue wavelength band,
wherein the second illumination light group includes second red light with a second red wavelength band, and
wherein the processor is configured to:
obtain:
a green image corresponding to the green light based on the image captured by the image sensor in the first frame;
a first blue image corresponding to the first blue light based on the image captured by the image sensor in the first frame; and
a second red image corresponding to the second red light based on the image captured by the image sensor in the second frame; and
generate a green channel image based on the green image, the first blue image and the second red image.

15. The endoscope apparatus according to claim 10, wherein the first red wavelength band has a peak wavelength at 600 nm±20 nm.

16. The endoscope apparatus according to claim 14, wherein the first blue wavelength band has a peak wavelength at 415 nm±20 nm.

17. The endoscope apparatus according to in claim 10, wherein the processor is configured to:
obtain:
a green image corresponding to the green light based on the image captured by the image sensor in the first frame; and
a first red image corresponding to the first red light based on the image captured by the image sensor in the first frame; and
extract a feature amount associated with a structure of an object, on the basis of the green image and the first red image.

18. The endoscope apparatus according to claim 17, wherein the processor is configured to combine the feature amount into the green image to highlight the structure of the object in the green image.

* * * * *